United States Patent [19]
Kroll et al.

[11] Patent Number: 5,411,526
[45] Date of Patent: May 2, 1995

[54] IMPROVED IMPLANTABLE DEFIBRILLATOR SYSTEM FOR PRODUCING TRUE-VOLTAGE-PULSE WAVEFORMS

[75] Inventors: Mark W. Kroll, Minnetonka; Charles G. Supino, Arden Hills; Theodore P. Adams, Edina; Dennis A. Brumwell, Bloomington, all of Minn.

[73] Assignee: Angeion Corporation, Plymouth, Minn.

[21] Appl. No.: 856,733

[22] Filed: Mar. 24, 1992

[51] Int. Cl.⁶ .............................................. A61N 1/00
[52] U.S. Cl. .............................................. 607/5
[58] Field of Search ................... 128/419 D; 607/5, 7

[56] References Cited

U.S. PATENT DOCUMENTS

| | | | |
|---|---|---|---|
| 3,258,013 | 6/1966 | Druz | 128/419 D |
| 4,090,519 | 5/1978 | Pantridge et al. | 128/419 D |
| 4,821,723 | 4/1989 | Baker, Jr. et al. | 607/7 |
| 4,821,723 | 4/1989 | Baker, Jr. et al. | 128/419 D |
| 4,850,357 | 7/1989 | Bach, Jr. | 128/419 D |
| 4,850,357 | 7/1989 | Bach, Jr. | 28/419 D |
| 5,083,562 | 1/1992 | de Coriolis et al. | 607/7 |

OTHER PUBLICATIONS

J. L. Prevost and F. Batelli, "Sur quelques effets des descharges electriques sur le couer des mammifers," *Comptes rendus hebdomadaires des seances de l'Academie des sciences*, vol. 129, p. 1267, 1899.

A. C. Guyton and J. Satterfield, "Factors concerned in defibrillation of the heart, particularly through the unopened chest," *Am J of Physiology*, vol. 167, p. 81, 1951.

J. C. Schuder, G. A. Rahmoeller, and H. Stoeckle, "Transthoracic ventricular defibrillation with triangular and trapezoidal waveforms," *Circ Res*, vol. 19, pp. 689–694, Oct. 1966.

W. A. Tacker, L. A. Geddes, J. McFarlane, et al, "Optimum current duration for capacitor-discharge defibrillation of canine ventricles," *J Applied Physiology*, vol. 27 #4, pp. 480–483, Oct. 1969.

J. C. Schuder, H. Stoeckle, J. A. Wes, et al., "Transthoracic ventricular defibrillation in the dog with truncated and untruncated exponential stimuli," *IEEE Trans. Biom. Eng.*, vol. BME-18 #6, pp. 410–415, Nov. 1971.

P. S. Chen, P. D. Wolf, and F. J. Claydon, "The potential gradient field created by epicardial defibrillation electrodes in dogs," *Circulation*, vol. 74, pp. 626–635, Sep. 1986.

M. Mirowski, M. M. Mower, W. S. Staewen, et al., "Standby automatic defibrillator," *Arch. Int. Med.*, vol. 126, pp. 158–161, Jul. 1970.

J. C. Schuder, H. Stoeckle, J. A. West et al., "Ventricular defibrillation in the dog with a bielectrode intravascular catheter," *Arch. Int. Med.*, vol. 132, pp. 286–290, Aug. 1973.

M. Mirowski, M. M. Mower, V. L. Gott, et al, "Feasibility and effectiveness of low-energy catheter defibrillation in man," *Circulation*, vol. 47, pp. 79–85, Jan. 1973.

*Primary Examiner*—Lee S. Cohen
*Assistant Examiner*—Marianne Parker
*Attorney, Agent, or Firm*—Patterson & Keough

[57] ABSTRACT

The first embodiment of the present invention repositions the shunt thyristor used in the monophasic-waveform generator of the prior art so that it discharges the main capacitor through a series thyristor, thus increasing current through it briefly, rather than reducing current through it. The result of this arrangement is that the node between the series thyristor and the heart is pulled rapidly to a low voltage, causing the shunt switch to discharge the cardiac capacitance, as well as the main capacitance. The consequence is that discharging the cardiac capacitance requires a reversal of current in the heart, which enhances the heart-stimulating effect of the defibrillating waveform. The resulting true-voltage-pulse waveform has an efficacy approximating that of a biphasic waveform and is achieved with a circuit no more complex than that used to generate a monophasic waveform. A second and alternative embodiment of the present invention is a defibrillation system comprising a switching-bridge circuit, augmented by a zener diode and a rectifier diode, that is capable of delivering on demand any one of the waveforms known as monophasic, biphasic, and true-voltage-pulse waveforms.

5 Claims, 3 Drawing Sheets

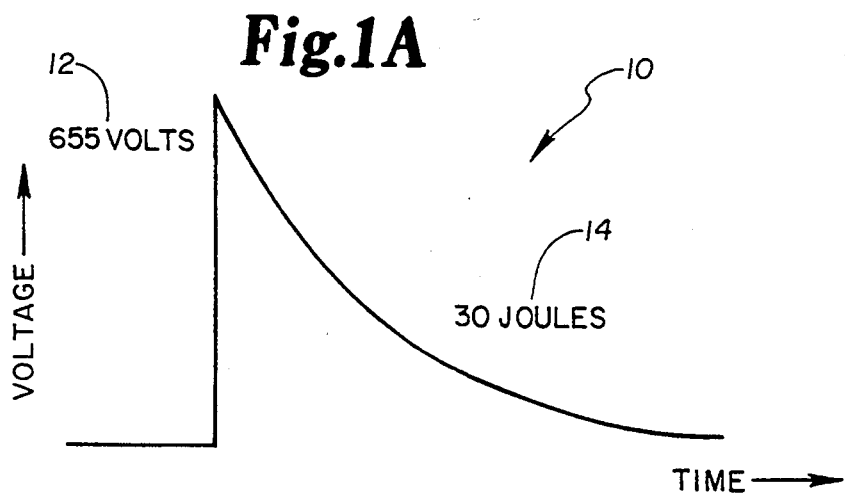
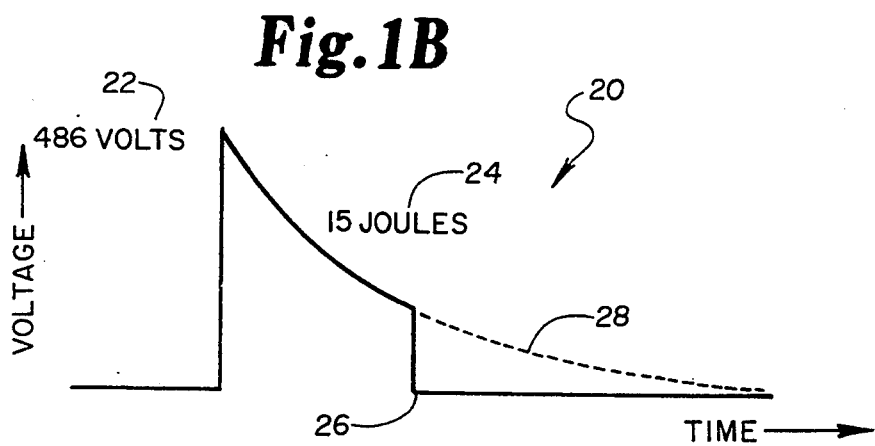
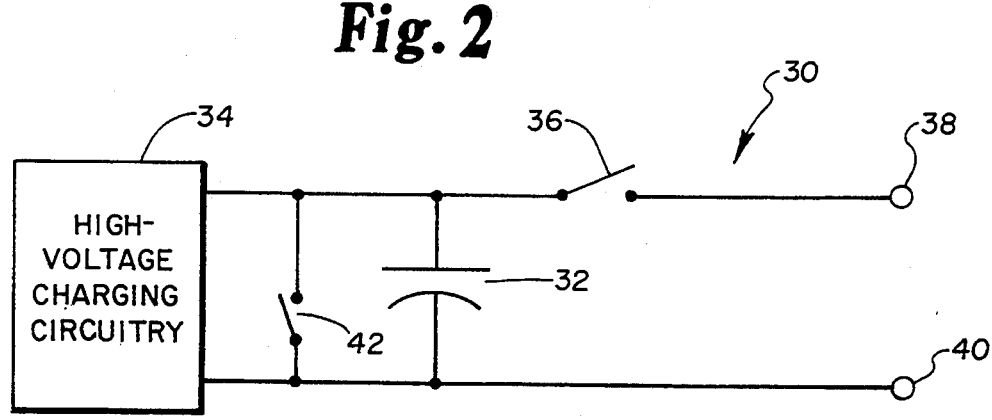

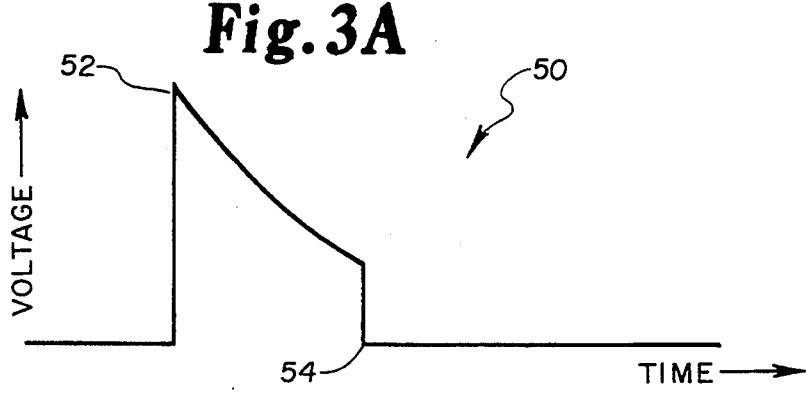
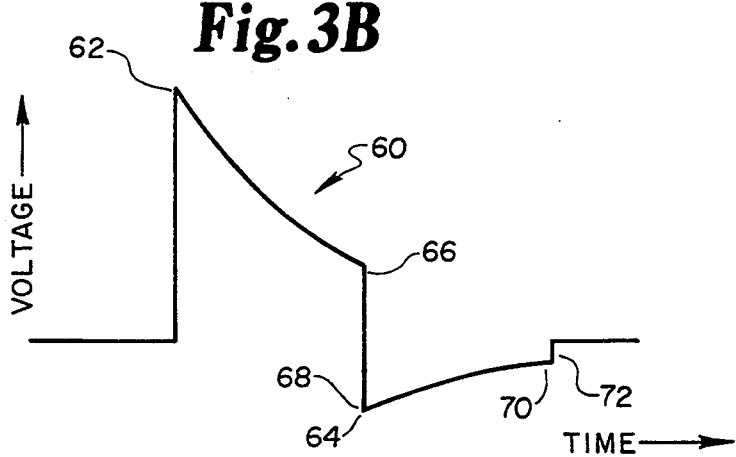
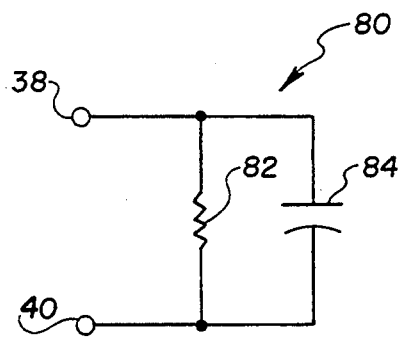
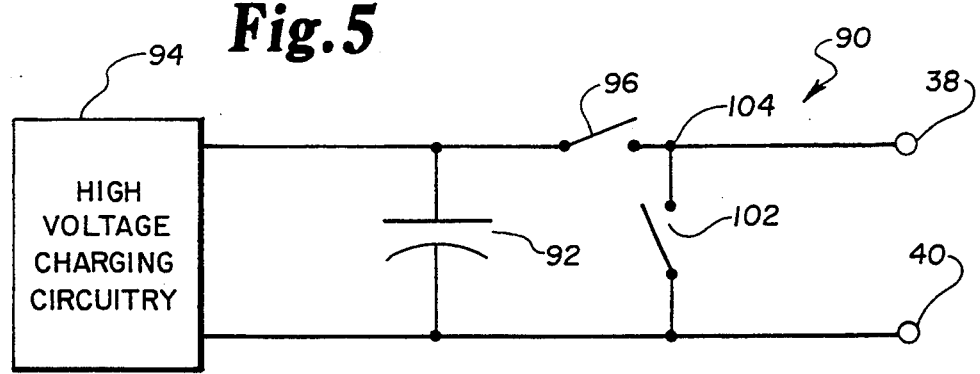

IMPROVED IMPLANTABLE DEFIBRILLATOR SYSTEM FOR PRODUCING TRUE-VOLTAGE-PULSE WAVEFORMS

BACKGROUND OF THE INVENTION

1. Field of the Invention

The present invention relates generally to defibrillation methods, and more particularly, to a system that is able to deliver a true voltage pulse to the heart from a charged capacitor.

2. Description of the Prior Art

Defibrillation, or causing the cessation of chaotic and uncoordinated contraction of the ventricular myocardium by application of an electrical direct current and voltage, in its most primitive form, goes back to the last century. [J. L. Prevost and F. Batelli, "Sur Quelques Effets des Descharges Electriques sur le Couer des Mammifers", *Comptes Rendus Hebdomadaires des Seances de L'Acadmie des Sciences*, Vol. 129, p. 1267, 1899.] Because of the large currents required for defibrillation, large-area electrodes are employed. [A. C. Guyton and J. Satterfield, "Factors Concerned in Defibrillation of the Heart, Particularly through the Unopened Chest", *Am J of Physiology*, Vol 167, p. 81, 1951.]

For reasons of simplicity and compactness, capacitor-discharge systems are almost universally used in defibrillation. The discharge of a capacitor C through a resistance R results in a pulse that is a declining exponential function, with a characteristic time given by the product RC. But it has also been recognized for some time that the long-duration, low-amplitude "tail" of the capacitor-discharge pulse is detrimental. [J. C. Schuder, et al., "Transthoracic Ventricular Defibrillation with Triangular and Trapezoidal Waveforms", *Circ. Res.*, Vol. 19, p. 689, October 1966; W. A. Tacker, et al., "Optimum Current Duration for Capacitor-discharge Defibrillation of Canine Ventricles", *J. Applied Physiology*, Vol 27, p. 480, October, 1969.] The exact reason for this detrimental effect is not known, although plausible speculations exist, with one possibility being that field heterogeneities cause arrythmias in significantly large regions of the heart. [P. S Chen, et al., "The Potential Gradient Field Created by Epicardial Defibrillation Electrodes in Dogs", *Circulation*, Vol. 74, p. 626, September 1986.] A convenient way to eliminate the low-amplitude "tail" of a capacitor discharge is by switching, which is to say, simply opening the capacitor-load circuit after a predetermined time, or else when voltage has fallen to a particular value. For this reason, the time-truncated capacitor discharge has been extensively used after its effectiveness was first demonstrated. [J. C. Schuder, et al., "Transthoracic Ventricular Defibrillation in the Dog with Truncated and Untruncated Exponential Stimuli", *IEEE Trans Biom. Eng.*, Vol. BME-18, p. 410, November 1971.]

The defibrillation effectiveness of time-truncated capacitor discharges can be convincingly shown by comparing an untruncated waveform and a truncated waveform of equal effectiveness. The full-discharge waveform of FIG. 1A was generated by charging a 140-F capacitor to 655 V, for an energy delivery of 30 J. But the truncated waveform shown in FIG. 1B, known in the art as a monophasic waveform, was equally effective for defibrillation in spite of having only half the energy, and a lower initial voltage. Similar results have been obtained for the case of dogs using a catheter electrode and a subcutaneous patch [M. Mirowski, et al., , "Standby Automatic Defibrillator", *Arch Int. Med.*, Vol. 126, p. 158, July 1970.], as well as with a dual-electrode intraventricular catheter. [J. C. Schuder, et al., "Ventricular Defibrillation in the Dog with a Bielectrode Intravascular Catheter", *Arch Int. Med.*, Vol. 132, p. 286, August 1973.] The latter electrode arrangement was also used to demonstrate the point for the case of man. [M. Mirowski, et al., "Feasibility and Effectiveness of Low-energy Catheter Defibrillation in Man", *Circulation*, Vol 47, p 79, January 1973.]Such demonstrations that compact capacitor-storage systems could be used with effectiveness paved the way for implantable defibrillator systems.

In spite of the dramatic results obtained with time-truncated capacitor-discharge defibrillator systems, the waveform specifications have not been systematically optimized. Present art arranges to have external current to the heart go to zero at the time of truncation, a condition that significant evidence shows to be less than optimum. The zero-current condition is a result of the switch configuration conventionally used for generating a monophasic pulse, which is shown in FIG. 2. Each switch symbol represents a solid-state device, usually a thyristor. This device, earlier known as a "silicon controlled rectifier", exhibits turn-on gain, but not turn-off gain. That is, a relatively low-power control pulse applied through an extra terminal is able to switch the device from its blocking, or OFF, condition to its conducting, or ON, condition. Turning the device off again requires reducing the current through it, or voltage across it, to a low value. The diagram of FIG. 2 is highly schematic, omitting such known details as small current-limiting resistors.

In operation of this system, the capacitor C is maintained in the charged condition by the high-voltage circuitry at the left. Then, the series switch 36 of FIG. 2 is turned ON to initiate the monophasic pulse, causing the capacitor C to commence its discharge through the heart. At the truncation point, the shunt switch 42 is closed, causing the capacitor C to be discharged rapidly. Consequently, the SCR will be back-biased and will turn off. The current from the capacitor to the heart will also decline rapidly, along with the decline in voltage, approaching zero, and reaching zero after the series switch 36 opens. The result is the monophasic waveform illustrated in FIG. 3A.

The prior art has sometimes used devices other than thyristors for the high-current switching. There are, for example, variations on the thyristor that exhibit a measure of turn-off gain, as well as turn-on gain, but these require more elaborate control circuitry than does the standard thyristor. Also there are available more complex devices that are in effect compound transistors, combining MOSFET and BJT principles, thus requiring less straightforward design. Pure field-effect devices, such as power MOSFETs, can handle currents of the order of those delivered to the heart in a defibrillation pulse. But note that the capacitor-discharging function of the shunt switch 42 involves much large instantaneous currents than that. Devices based upon carrier injection, such as the thyristor, are better adapted to this high-current requirement than are MOSFETs, which are essentially resistive devices.

It is known in the prior art that the heart-cell stimulation resulting from high-current delivery can be augmented by the sudden removal of current, a phenomenon known as "break stimulation." It is also known that break stimulation is further enhanced by actually reversing current, rather than simply reducing it to zero. A demonstration of this was provided when workers studying the effectiveness of multiple defibrillation pulses observed that a waveform consisting of a pair of contiguous pulses of opposite polarity was more effective than a monophasic pulse. Such a waveform is known as biphasic, and is well-established in the prior art. [Bach, U.S. Pat. No. 4,850,537, and Baker, U.S. Pat. No. 4,821,723.] The biphasic waveform is illustrated in FIG. 3B. Unfortunately, the prior-art biphasic system requires elaborated switching and control arrangements. Hence there is a need for a system that is capable of delivering current reversal with circuitry as simple as that of the monophasic system.

SUMMARY OF THE INVENTION

The general purpose of the present invention is a true voltage waveform in which the output voltage is determined by the generating device throughout the pulse and its termination phase. This is differentiated from the conventional defibrillation pulse which is voltage determined during the main part of the pulse, but is current determined (namely to a zero current) during the termination phase.

The fundamental distinction between the prior art and the present invention is this: In the prior-art circuit, the discharging capacitor and the heart remain connected in parallel as long as the series switch is closed, which is to say, until the current from the capacitor to the heart has dropped to very near zero or zero. The shunt switch that discharges the capacitor is connected to a node lying between the capacitor and the high-voltage power supply that charges the capacitor in preparation for discharge. In the present invention, on the other hand, the shunt switch is connected to a node lying between the capacitor and the heart. A crucial fact here is that the heart can be modeled on a lumped-element basis as a capacitor 84 and resistor 82 in parallel, as shown in FIG. 4, with the cardiac capacitance comprising electrode, cell, and fluid capacitance. In truth, of course, both the resistance of the heart's tissues and its capacitance are distributed properties, so that lumped-element modeling constitutes a primitive approximation, but one that clarifies the essential point here.

The point is that the shunt switch discharges both the discharge capacitance 92 and the cardiac capacitance 84 simultaneously and independently. This operation can be seen clearly in the circuit of the present invention that is represented schematically in FIG. 5. In this circuit, the shunt switch 102 is able to reduce the voltage at the node intermediate between the two capacitances to near zero, causing a true reversal of current through the heart electrodes. Because voltage control is being exerted here, the invention has been termed true-voltage-pulse defibrillation.

The voltage and current relationships here are not totally obvious, and warrant a more detailed description. The current flowing into the heart at the time of truncation reverses and flows out of the heart at the time when voltage across the shunt switch 102 equals the remnant voltage on the heart's capacitance, 84, with a result that is depicted in FIG. 6. The initial portion of the waveform approximates that of the conventional monophasic pulse, but negative current follows the completion of truncation as the shunt switch 102 discharges the cardiac capacitance 84. The heart's resistance 82, of course contributes to discharging, but its value of about 50 ohms means that the shunt switch 102 with an effective resistance of only a few ohms does most of the discharging.

There are other clear distinctions between the prior art and the present invention. For one, note that in FIG. 2, the series switch 36 carries a current that declines steeply and monotonically after the point of truncation. In FIG. 5, on the other hand, the series switch 96 carries a current spike approximating the spike that passes through the shunt switch 102 after truncation. There is yet another way of describing the difference between the two systems, and that is in terms of the impedance seen by the heart as it "looks into" the source of a two-switch defibrillation pulse. In the monophasic case of the prior art, the pulse source has low impedance and delivers a voltage in the interval from triggering to truncation; then the source abruptly converts to current control, which means it has high impedance during the truncation process. In the true-voltage-pulse case of the present invention, though, the source controls voltage throughout the pulse, retaining its low impedance.

An extension of the present invention is the versatile circuit shown in FIG. 7 that is capable of delivering a conventional monophasic waveform, a conventional biphasic waveform, or the true-voltage-pulse waveform of the present invention. The diagram indicates the heart electrodes 146 and 148, the discharge capacitor 132, four primary switches, 134–140, a rectifier diode 142, and a zener diode 144. For the case of the monophasic waveform, the series switches 134 and 140 are turned ON to initiate the pulse, and then are turned OFF by conventional means to truncate the pulse.

To generate the biphasic waveform, the series switches 134 and 140 are turned ON to initiate the pulse, and then are turned OFF by conventional means at the polarity-reversal point. At the same point the switches 136 and 138 are turned on simultaneously, and then are turned off to terminate the waveform. Thus, the circuit shown constitutes a four-switch bridge of the kind that is standard for generating biphasic waveforms. During the first part of the waveform, the right-hand heart electrode is near zero voltage, so the rectifier diode 142 and zener diode 144 play no part; and during the second part of the waveform, the same heart electrode is positive, so that the rectifier diode 142 effectively opens its loop.

Generation of the true-voltage-pulse waveform starts out like the monophasic case, with the closing of the switches 134 and 140, whereupon current passes rightward through the heart. At the truncation point, those two switches 134 and 140 are left ON, and switch 136, now in combination with switch 134, a shunt switch, discharges the capacitor 132 and pulls the left-hand heart electrode 38 rapidly to zero voltage. The discharging of the cardiac capacitance that immediately follows requires a leftward current through the heart, a current carried by zener diode 144 and rectifier 142, because zener diode 144 is reverse-biased by the negative voltage on the right-hand cardiac electrode 148. A thyristor is open in reverse bias. The negative voltage on the right-hand electrode 40 is limited by zener diode 144 to a small value, such as minus six volts.

One significant aspect and feature of the present invention is a defibrillation waveform generated by a relatively simple circuit that undergoes a reversal of current and voltage polarity at the time of pulse truncation.

Another significant aspect and feature of the present invention is a shunt switch connected to a node lying between the defibrillation-discharge capacitor and the heart.

Still another significant aspect and feature of the present invention is a defibrillation waveform constituting a true voltage pulse.

Yet another significant aspect and feature of the present invention is a defibrillation waveform generator that constitutes a low-impedance source throughout the delivery of the defibrillation pulse.

An additional significant aspect and feature of the present invention is a circuit comprising only four primary switches that is capable of delivering monophasic, biphasic, and true-voltage waveforms. A true voltage waveform is one in which the output voltage is determined by the generating device throughout the pulse and its termination phase. This is differentiated from the conventional defibrillation pulse which is voltage determined during the main part of the pulse, but is current determined (namely to a zero current) during the termination phase.

A further significant aspect and feature of the present invention is a defibrillation system of smaller size but equal effectiveness as compared to a similar system of the prior art.

Having thus described the embodiments and features of the present invention, it is a principal object of the present invention to provide a circuit that is able to deliver a waveform that undergoes a reversal of current and voltage polarity at the time of pulse truncation.

One object of the present invention is to employ voltage control of a defibrillation pulse throughout the entire pulse.

Another object of the present invention is to provide a defibrillation waveform generator that constitutes a low-impedance source throughout the delivery of the defibrillation pulse.

Still another object of the present invention is to provide a circuit including only four primary switches that is capable of delivering monophasic, biphasic and true-voltage waveforms. A true voltage waveform is one in which the output voltage is determined by the generating device throughout the pulse and its termination phase. This is differentiated from the conventional defibrillation pulse which is voltage determined during the main part of the pulse, but is current determined (namely to a zero current) during the termination phase.

A further object of the present invention is to reduce the size and complexity of the circuit required to deliver a waveform of a given degree of defibrillation efficacy, thus reducing system size and volume, and enhancing implantation flexibility.

BRIEF DESCRIPTION OF THE DRAWINGS

Other objects of the present invention and many of its attendant advantages will be readily appreciated as the invention becomes better understood by reference to the following descriptions, when considered in connection with the accompanying drawings in which like reference numerals designate like parts throughout the figures thereof, and wherein:

FIG. 1A illustrates a particular voltage-time waveform of a capacitor discharged through a resistor;

FIG. 1B illustrates a particular voltage-time waveform of a time-truncated pulse, produced by discharging a capacitor through a resistor and terminating the pulse by switching, with this pulse delivering half the energy of that in FIG. 1A;

FIG. 2 illustrates a circuit of the prior art used for generating a monophasic waveform;

FIG. 3A illustrates a monophasic waveform of the prior art;

FIG. 3B illustrates a biphasic waveform of the prior art;

FIG. 4 illustrates a lumped-element equivalent-circuit model of the heart;

FIG. 5 illustrates an electrical circuit schematic diagram of the present invention that delivers a true-voltage-pulse waveform;

DETAILED DESCRIPTION OF THE ART

Figure 6:
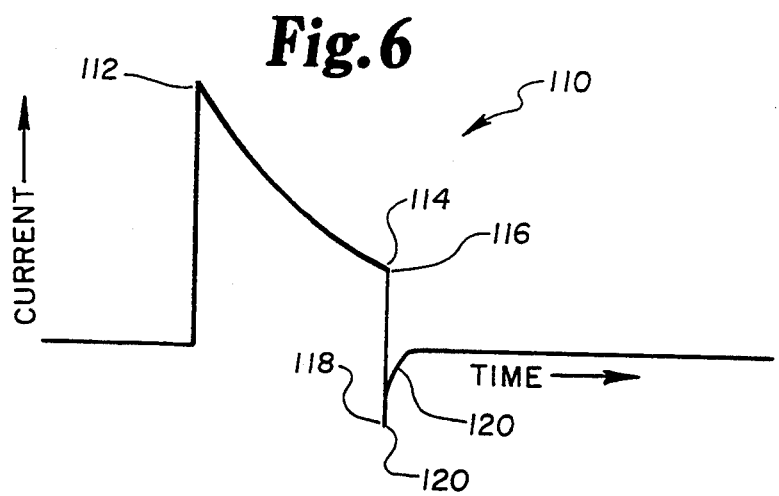
FIG. 6 illustrates the current in a true-voltage-pulse waveform of the present invention.

FIG. 1A illustrates a particular voltage-time defibrillation waveform 10 of a capacitor discharged through a resistor, incorporating a particular initial voltage 12, and a particular energy 14 delivered from the capacitor to the resistor.

FIG. 1B illustrates a particular voltage-time defibrillation waveform 20 of a capacitor discharged through a resistor, incorporating a particular initial voltage 22. A particular energy 24 is delivered from the capacitor to the resistor, and also incorporating time-truncation of the pulse, produced by terminating the pulse through switching at the particular time 26, thus eliminating the tail 28 of the pulse. This particular pulse delivers half the energy of the particular pulse in FIG. 1A.

FIG. 2 illustrates a circuit 30 of the prior art for generating a monophasic defibrillation waveform, including a discharge capacitor 32 that is charged by the high-voltage power supply 34. The capacitor 32 is discharged by the closing of the series switch 36 to initiate the monophasic pulse, delivering voltage and current to the cardiac electrodes 38 and 40 of FIG. 4 until the shunt switch 42 closes at the truncation time. This causes the capacitor 32 to be discharged, and in turn causes current through the series switch 36 to decline rapidly to such a point that the switch 36 opens.

FIG. 3A illustrates a monophasic defibrillation waveform 50 of the prior art with a particular initial voltage 52 and having a particular truncation time 54.

FIG. 3B illustrates a biphasic defibrillation waveform 60 of the prior art with a particular initial voltage 62, a particular polarity-reversal time 64, and voltage 66, at which the current is switched so that the opposite voltage of the same magnitude 68 is applied to the heart, and with a particular time 70 and voltage 72 at which the waveform is concluded.

FIG. 4 presents a lumped-element equivalent-circuit model 80 of the heart, including a cardiac resistance 82 and a cardiac capacitance 84 in parallel, as well as cardiac electrodes 38 and 40.

DETAILED DESCRIPTION OF THE PREFERRED EMBODIMENTS

FIG. 5 illustrates an electrical circuit schematic diagram 90 of the present invention for generating a true-voltage-pulse defibrillation waveform, including a discharge capacitor 92 that is first charged by the high-voltage power supply 94, and that is then discharged by the closing of the series switch 96 to initiate the true-voltage-pulse waveform, delivering voltage and current to the cardiac electrodes 38 and 40 of FIG. 4 until the shunt switch 102 closes at the truncation time, thereby causing the node 104 to approach zero voltage rapidly, and in turn, causing rapid and independent discharge of both the capacitor 92 and the cardiac capacitor 84 of FIG. 4. A true voltage waveform is one in which the output voltage is determined by the generating device throughout the pulse and its termination phase. This is differentiated from the conventional defibrillation pulse which is voltage determined during the main part of the pulse, but is current determined (namely to a zero current) during the termination phase.

FIG. 6 illustrates a true-voltage-pulse waveform 110 of the present invention, with a particular initial current 112, a particular truncation time 114, and current 116, at which time the current is switched so that an opposite current 118 is applied to the heart, which is followed by a negative current tail 120.

DESCRIPTION OF THE FIRST ALTERNATIVE EMBODIMENT

Figure 7:
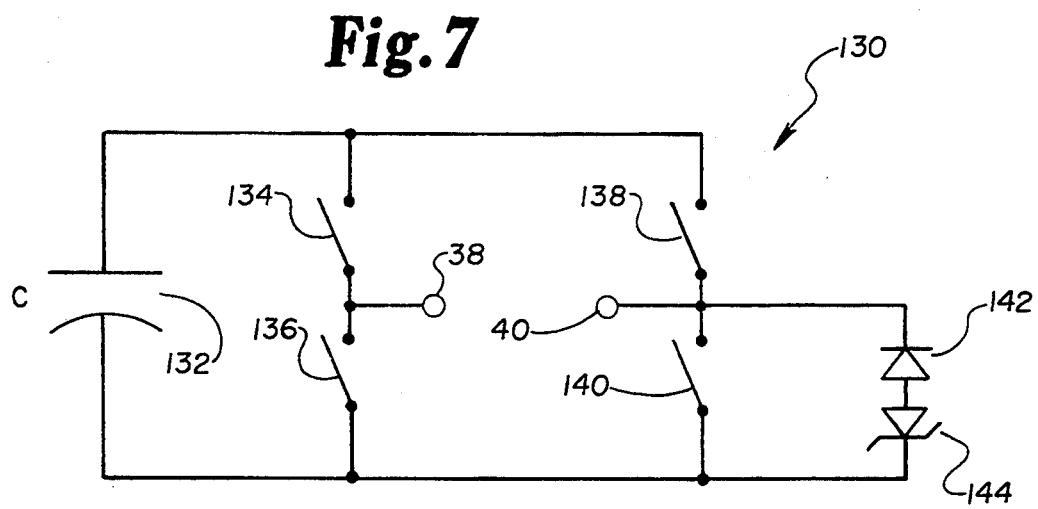
FIG. 7, a first alternative embodiment, illustrates an electrical circuit schematic diagram of the present invention that delivers a monophasic, biphasic, and true-voltage-pulse waveforms; and, FIG. 8, a second alternative embodiment, illustrates an electrical circuit schematic diagram.

FIG. 7, a first alternative embodiment, illustrates an electrical circuit schematic diagram 130 of the present invention that is able to deliver monophasic, biphasic, and true-voltage-pulse waveforms. The circuit includes a discharge capacitor 132, primary switches 134, 136, 138, and 140, a rectifier diode 142, a zener diode 144, which in the appropriate switching combination are able to deliver a selected one of the three waveforms to the cardiac electrodes 38 and 40 of FIG. 4.

MODE OF OPERATION

The first embodiment of the present invention, FIG. 5, configures the components used in a circuit of the prior art by repositioning the switch used in the monophasic-waveform generator of the prior art to reduce current through the switch to a point where the switch turns off. The switch does so in the prior-art case by quickly discharging the main capacitor of the system.

In the circuit of the present invention, the switch also discharges the main capacitor, but does so through the switch, thus increasing current through it briefly, rather than reducing current through it. The benefit of this arrangement is that the node between the switch and the heart is pulled rapidly to a low voltage, causing the shunt switch to discharge the cardiac capacitance as well as the main capacitance. The consequence of discharging the cardiac capacitance in this manner is that this discharging requires a reversal of current in the heart, which enhances the heart-stimulating effect of the defibrillating waveform. The overall result of this circuit configuration is that a waveform with an efficacy approximating that of the biphasic waveform is achieved with a circuit no more complex than that used to generate a monophasic waveform.

An alternative embodiment of the present invention, FIG. 7, is the defibrillation system comprising a switching-bridge circuit, including a zener diode and a rectifier diode, that is capable of delivering on demand any one of the three waveforms known as monophasic, biphasic, and true-voltage-pulse waveforms.

DESCRIPTION OF THE SECOND ALTERNATIVE EMBODIMENT

Figure 8:
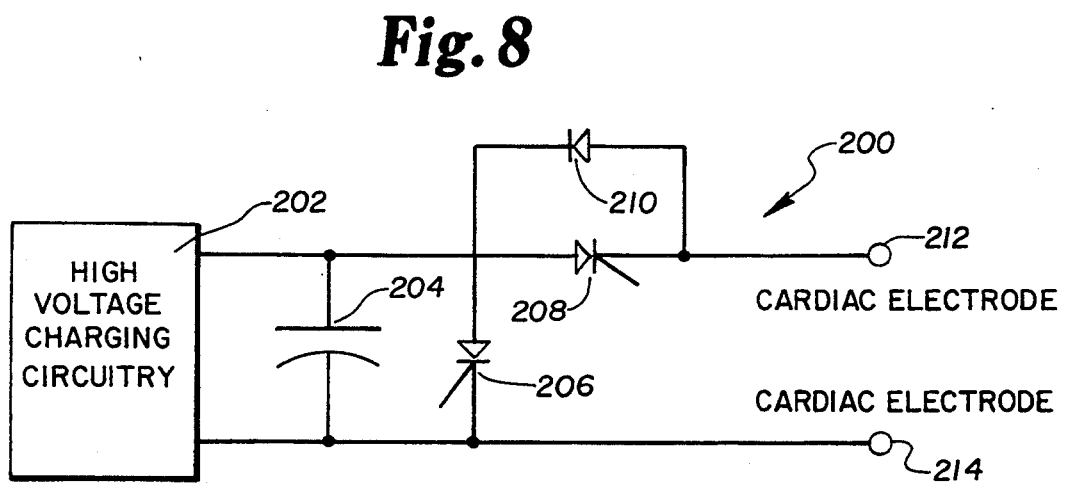

FIG. 8, a second alternative embodiment of the present invention, illustrates an electrical circuit schematic diagram including a diode 210 in reverse parallel with a series SCR 208. In normal operation, the series SCR is turned on and current is supplied to the heart. At the time of pulse truncation, the shunting SCR 206 is turned on which back biases the series SCR 208, and thus, turns it off. Hence, the heart quickly has the current brought to zero. The reverse parallel diode 216 conducts the reverse current after truncation. This brings the heart voltage to zero after truncation, thus resulting in a true-voltage waveform.

Various modifications can be made to the present invention without departing from the scope hereof.

We claim:

1. In an implantable defibrillatory system for producing a truncated capacitive-discharge biphasic countershock, the implantable defibrillator system being a self-contained human implantable device that includes a pulse-generating capacitor means for storing an electrical charge, means for internally charging the pulse-generating capacitor means, and means for selectively discharging the electrical charge in the pulse-generating capacitor means for a specified pulse duration as a biphasic countershock to be delivered through electrodes adapted for implantation in a human patient in response to a means for sensing of a myocardial arrhythmia in the human patient, the improvement comprising:

the means for selectively discharging the electrical charge including means for delivering the biphasic countershock as a true-voltage-pulse waveform in which an output voltage of the biphasic countershock is actively determined throughout the pulse duration, including both a switching phase during which an output polarity of the biphasic countershock is reversed and a termination phase during which the biphasic countershock is truncated.

2. The system of claim 1 wherein there is an impedance looking back through the electrodes and wherein the true voltage pulse waveform is generated by the means for selectively discharging the electrical charge such that the impedance is a low output impedance throughout the pulse duration.

3. The system of claim 1 wherein the means for delivering the countershock as a true-voltage-pulse waveform comprises:

a shunt switch connected to a node between the pulse-generating capacitor means and the electrodes through which the countershock is delivered to the heart.

4. In an implantable defibrillation system for producing a truncated capacitive-discharge countershock, the implantable defibrillator system being a self-contained human implantable device that includes a pulse-generating capacitor means for storing an electrical charge, means for internally charging the pulse-generating capacitor means, and means for selectively discharging the electrical charge in the pulse-generating capacitor means for a specified pulse duration as a countershock to be delivered through electrodes adapted for implantation in a human patient in response to a means for sensing of a myocardial arrhythmia in the human patient, the improvement comprising:

a shunt switch;

the electrodes having a first terminal in common with a first terminal of each of the pulse-generating capacitor means and said shunt switch;

the means for selectively discharging the electrical charge including a series switch connected between a second terminal of the pulse-generating capacitor means and a second terminal of the shunt switch; and the second terminal of the shunt switch connected to a node lying between the series switch and a second terminal of the electrodes, the node being a conductor circuit extending from the series switch to the second terminal of the electrodes, such that the means for selectively discharging the electrical charge selectively closes the shunt switch at the specified pulse duration to actively truncate the countershock.

5. The system of claim 4 wherein there is an impedance looking back through the electrodes and wherein the true voltage pulse waveform is generated by the means for selectively discharging the electrical such that the impedance is a low output impedance throughout the pulse duration.

* * * * *